United States Patent [19]

Carls et al.

[11] Patent Number: 5,702,460
[45] Date of Patent: Dec. 30, 1997

[54] REVISION FEMORAL TRIAL PROSTHESIS

[75] Inventors: Thomas A. Carls; Tony Melkent, both of Memphis, Tenn.; Leo A. Whiteside, Bridgeton, Mo.; Tim Vendrely, Memphis, Tenn.

[73] Assignee: Smith & Nephew, Inc., Memphis, Tenn.

[21] Appl. No.: 515,991

[22] Filed: Aug. 16, 1995

Related U.S. Application Data

[63] Continuation-in-part of Ser. No. 482,935, Jun. 7, 1995, which is a continuation-in-part of Ser. No. 389,100, Feb. 15, 1995, Pat. No. 5,609,642.

[51] Int. Cl.$^6$ .................................................. A61F 2/38
[52] U.S. Cl. ........................ 623/20; 606/79; 606/88
[58] Field of Search .......................... 623/18, 20, 23; 606/79, 80, 87, 88, 89, 102

[56] References Cited

U.S. PATENT DOCUMENTS

| | | | |
|---|---|---|---|
| 4,016,606 | 4/1977 | Murray et al. | 3/1.911 |
| 4,601,289 | 7/1986 | Chiarizzio et al. | 128/305 |
| 4,938,769 | 7/1990 | Shaw | 623/20 |
| 4,950,298 | 8/1990 | Gustilo et al. | 623/20 |
| 5,007,933 | 4/1991 | Sidebotham et al. | 623/20 |
| 5,019,103 | 5/1991 | Van Zile et al. | 623/20 |
| 5,080,675 | 1/1992 | Lawes et al. | 623/20 |
| 5,080,676 | 1/1992 | May | 623/20 |
| 5,137,536 | 8/1992 | Koshino | 623/20 |
| 5,194,066 | 3/1993 | Van Zile | 623/20 |
| 5,246,459 | 9/1993 | Elias | 623/20 |
| 5,258,032 | 11/1993 | Bertin | 623/20 |
| 5,326,359 | 7/1994 | Oudard | 623/20 |
| 5,342,367 | 8/1994 | Ferrante et al. | 606/86 |
| 5,417,693 | 5/1995 | Sowden et al. | 623/20 |

*Primary Examiner*—Randy C. Shay
*Attorney, Agent, or Firm*—Pravel, Hewitt, Kimball & Krieger

[57] ABSTRACT

A trial femoral prosthesis for use in knee joint replacement surgery includes a trial prosthesis body that is generally J-shaped. The prosthesis body provides a distal articulating surface and a proximal non-articulating surface. The articulating surface includes medial and lateral condylar portions, a distal portion, and an anterior portion. An elongated stem extends from the distal non-articulating surface for anchoring the trial prosthesis to the intramedullary canal of the patient's femur. Wedge trial insert members are connectable to the trial prosthesis body at the non-articulating surface. The inserts can be of different shape and different thicknesses and can be independently placed on opposite sides of the stem. However, the prosthesis body can be used independently without any inserts. The apparatus assists a surgeon who is going to revise a total knee that had been previously implanted. If a surgeon needs a wedge insert for the trial, a corresponding wedge is placed on the final knee implant. The trial prosthesis body and wedges each provide cutting edges that remove bone in the exact places in order to make the implant fit snugly. The cutting edges shave bone material when the surgeon drives the trial onto the distal femur. If bone needs to be removed in the distal area to accommodate a wedge insert, cutting guide slots are provided in the trial prosthesis body. If bone needs to be removed in the anterior or posterior chamfer area, angled chamfer cutting guide slots are provided in the trial prosthesis body.

54 Claims, 7 Drawing Sheets

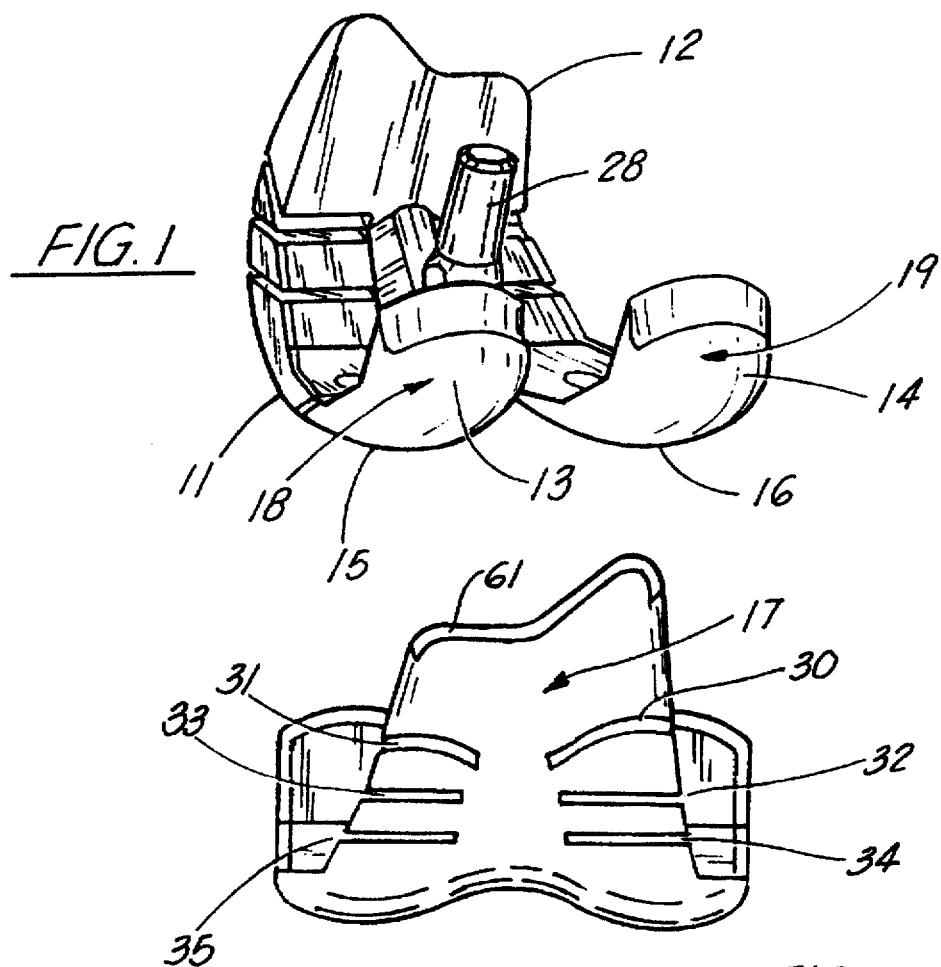
FIG. 1
FIG. 2
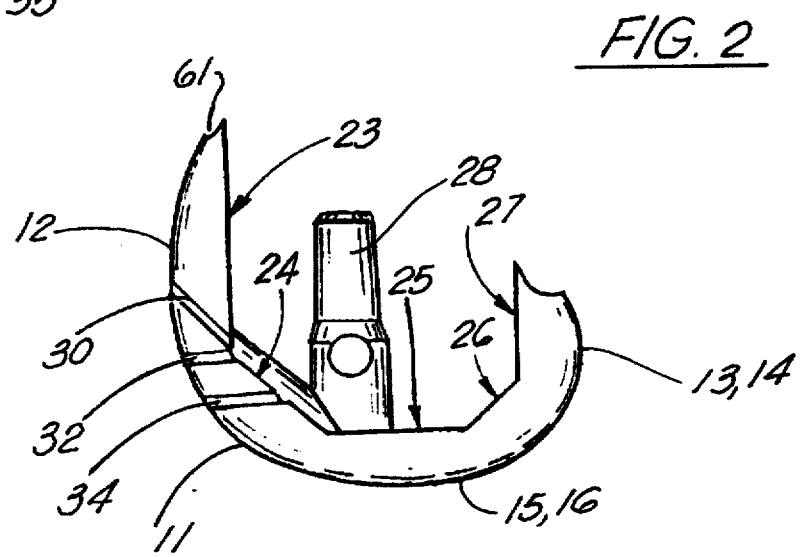
FIG. 3

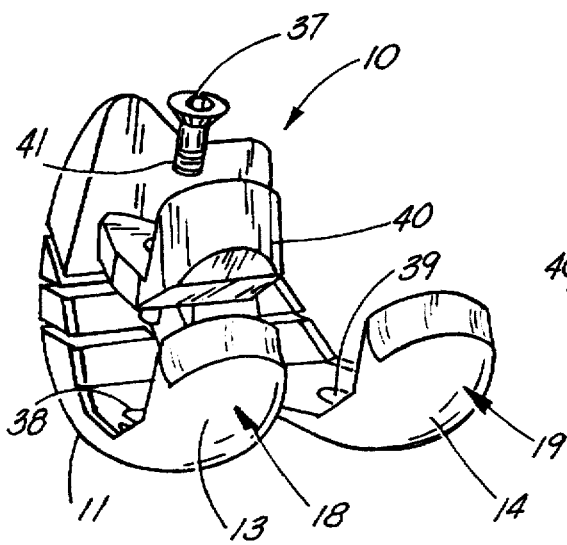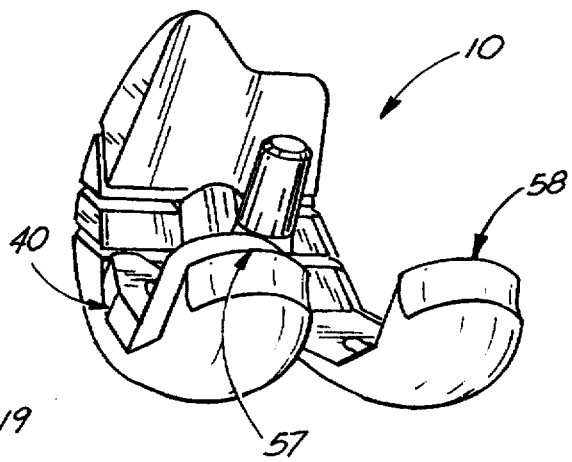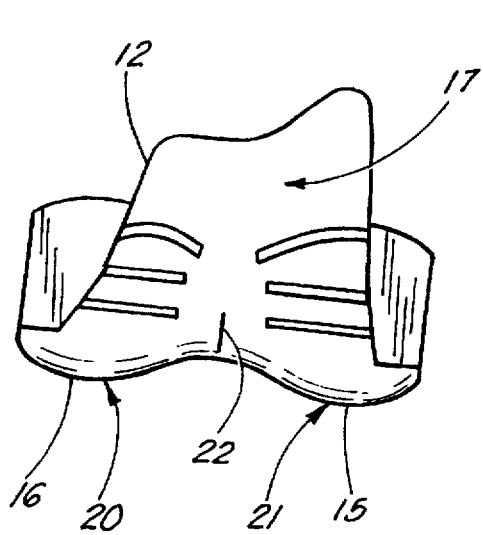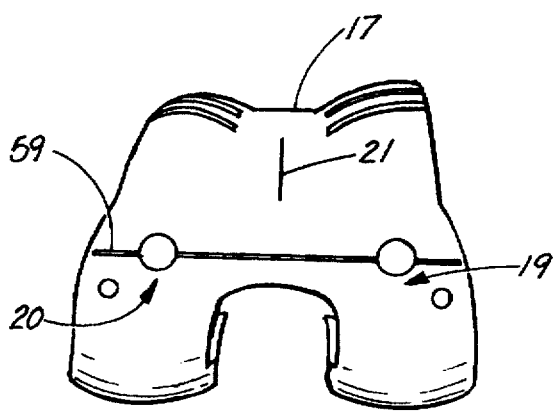

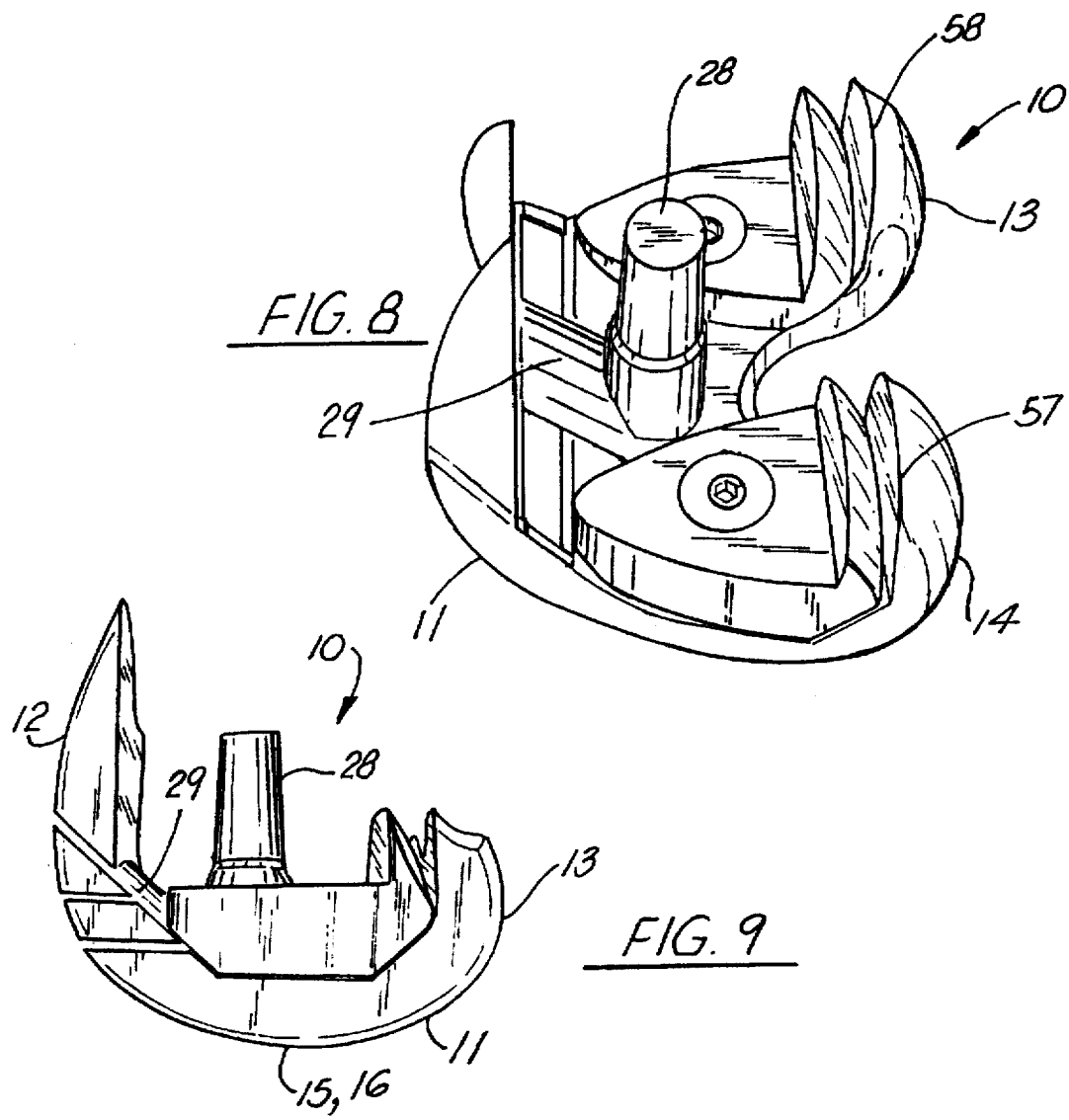
FIG. 8
FIG. 9
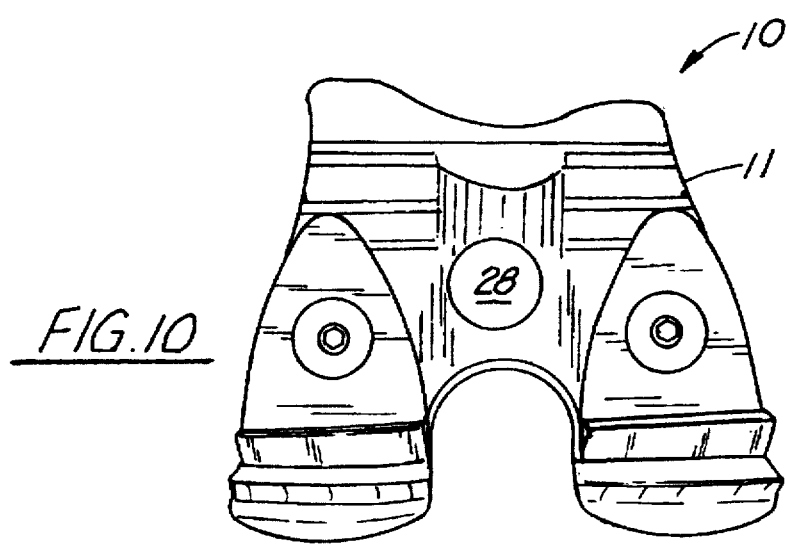
FIG. 10

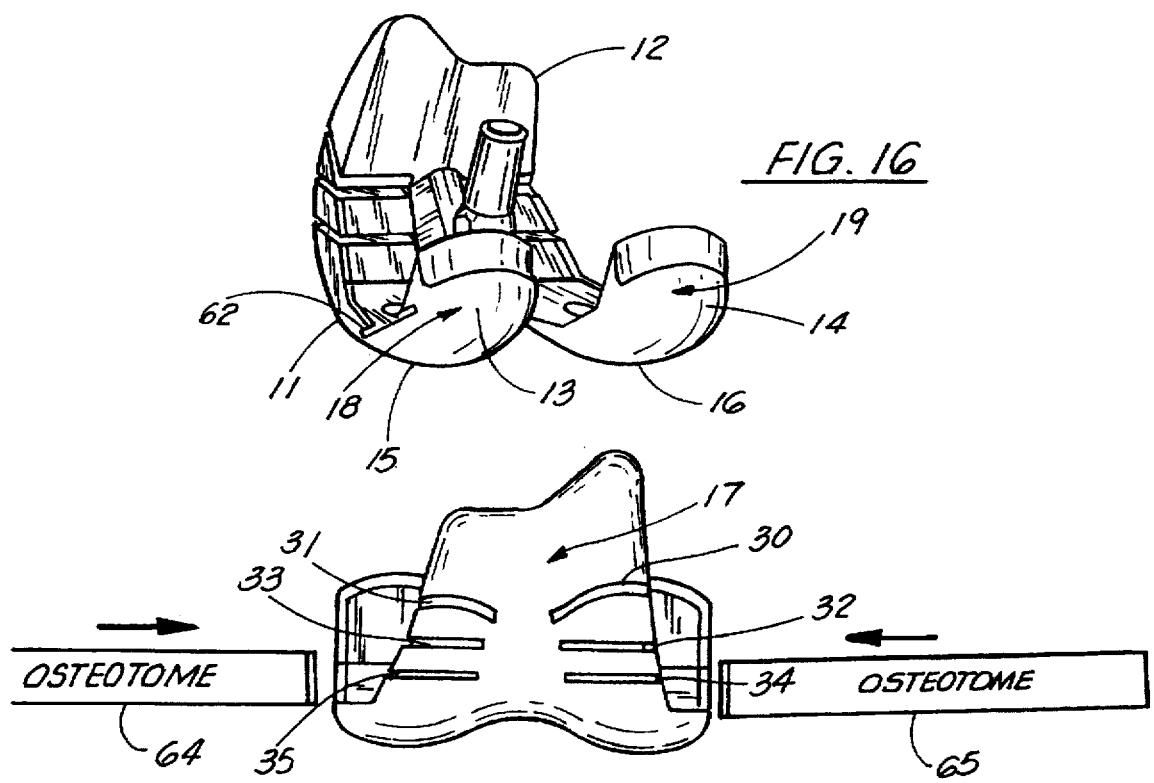
FIG. 16
FIG. 17
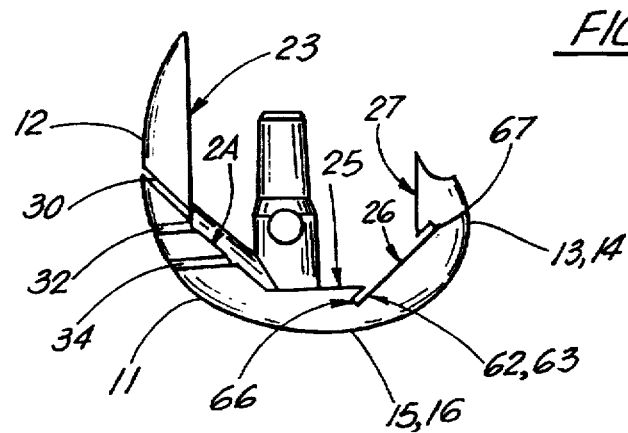
FIG. 18

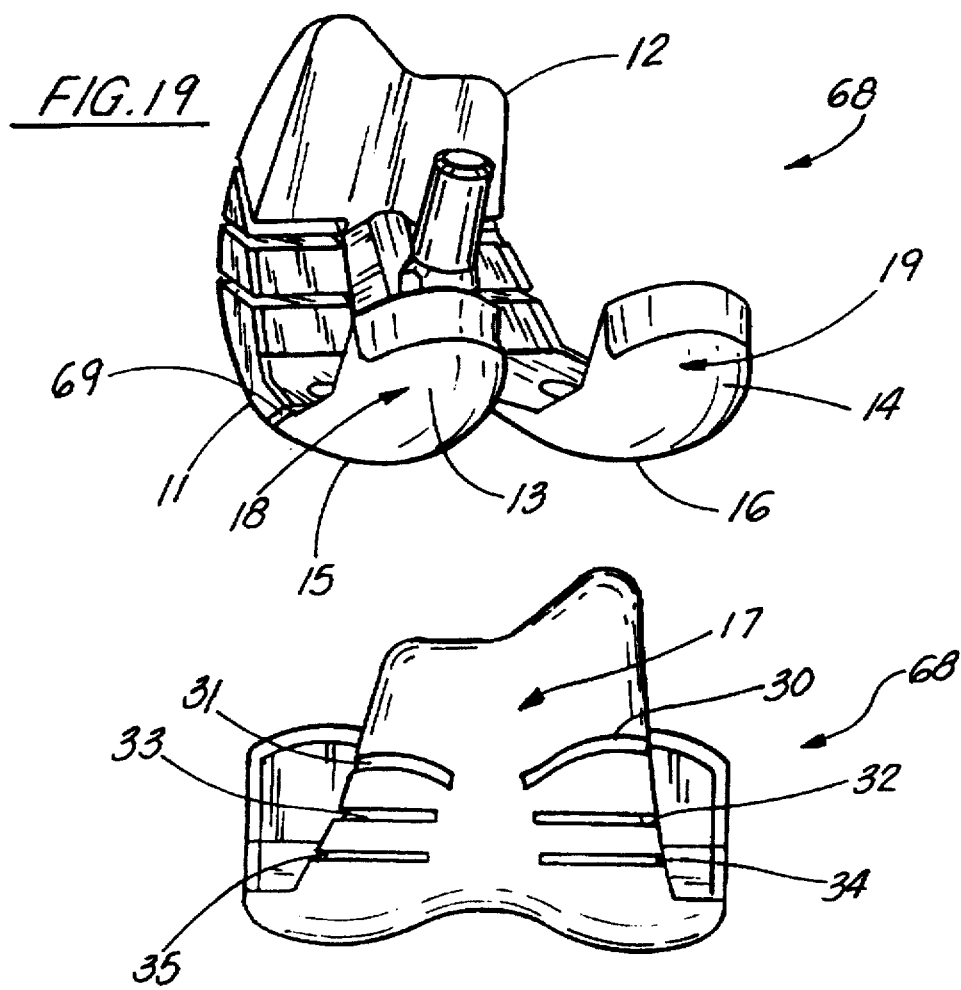
FIG. 19
FIG. 20
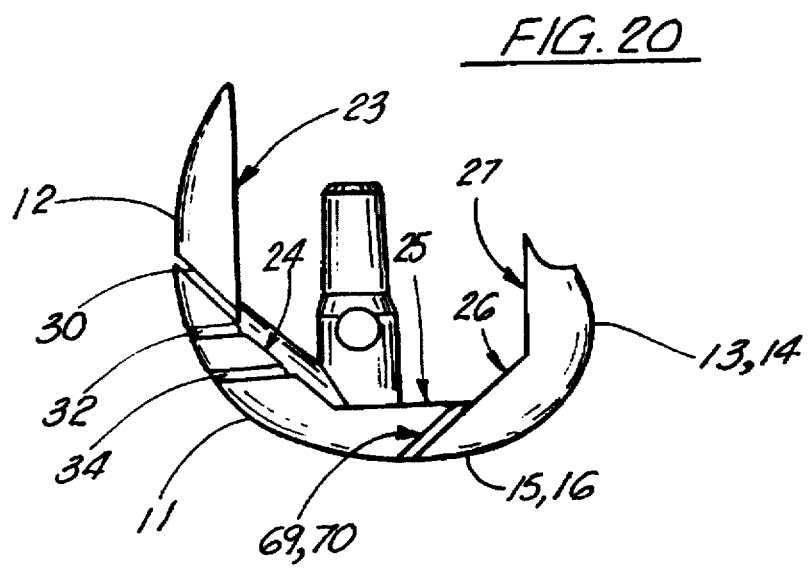
FIG. 21

REVISION FEMORAL TRIAL PROSTHESIS

CROSS REFERENCE TO RELATED APPLICATIONS

This is a continuation-in-part of copending U.S. patent application Ser. No. 08/482,935, filed Jun. 7, 1995, allowed, which is a continuation-in-part of U.S. patent application Ser. No. 08/389,100, filed Feb. 15, 1995, now U.S. Pat. No. 5,609,642, which is incorporated herein by reference.

BACKGROUND OF THE INVENTION

1. Field of the Invention

The present invention relates to orthopedic surgical instruments and surgical methods and particularly relates to an improved method and apparatus for assisting a surgeon to revise a previously implanted total knee implant. More particularly the present invention relates to an improved method and apparatus for installing a knee prosthesis with modular instrumentation that allows a surgeon to build a revision femoral trial prothesis using multiple trial wedge portions of different size and shape that can be butted to a prosthesis body. This "trial" not only allows the surgeon to evaluate the proper implant size, but it is also used to assist the surgeon in preparing the bone for implants and to correctly orient the implants in different planes.

2. General Background

In knee joint replacement surgery, a surgeon typically affixes prosthesis components to the patient's femur and tibia. These replacement components are typically known as the femoral component and the tibial component.

The femoral component is placed on a patient's distal femur after the surgeon makes a plurality of surgical cuts. One common type of femoral prothesis has a J-shape. A femoral prosthesis is usually metallic, having a highly polished outer femoral articulating surface.

A common type of tibial prosthesis uses a laterally extending tray that is shaped to conform to the patient's proximal tibia after the proximal tibia has been cut transversely by the surgeon. The tibia prosthesis also includes a stem or plug that extends generally perpendicular to the tray and from the center of the tray. The stem is placed in a surgically formed opening that extends into the patient's intramedullary canal from the transverse cut formed on the proximal tibia.

A plastic, polymeric insert is attached to the tibial tray. This insert provides a tibial articulating surface that articulates with the femoral articulating surface as the patient's tibia moves through a full range of motion with respect to the patient's femur.

One of the problems with knee joint replacement surgery is that of accurately fitting the patient. Each patient has a different bone structure and geometry. This is true in revision cases as well. Even though the surgeon uses x-rays to study a particular patient's anatomy at the knee, the surgeon does not have a perfect appreciation of the patient's anatomy until after the knee has been surgically exposed and the surgeon begins to make cuts on the femur and the tibia. In some revision cases, bone is deteriorated on one side of the patient's leg bone more than another.

Knee prosthetic components are not available in infinite sizes. The surgeon must examine the patient's anatomy, make the requisite surgical cuts and install prosthesis components that fit.

A number of prosthetic knee components have been patented. Some relate to femoral components and tibial components. Other patents have been issued that relate to cutting instrumentation for preparing the patient's distal femur or proximal tibia to receive a prosthetic knee component as part of knee joint replacement surgery.

The Whiteside U.S. Pat. No. 4,467,801, entitled "Method And Apparatus For Shaping A Proximal Tibial Surface", provides a method and apparatus for preparing the proximal surface of a tibia to receive a proximal tibial prosthesis employing a reamer/alignment guide which is used to internally locate the central long axis of the tibia and a plateau planar which cooperatively engages with a guide handle attached to the reamer/alignment guide to accomplish the shaping of the proximal tibial surface. The reamer/alignment guide has a rod portion extending into the interior of the tibial shaft whose central long axis corresponds with the central long axis of the tibia. The guide handle is concentric with that rod portion such that the plateau planar assumes the proper alignment with respect to the central long axis of the tibia such that the proximal tibial surface is shaped relative to that axis in a simple and accurate manner.

European Patent Application No. 0 122 669 discloses a guide for femoral neck osteotomy that comprises a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongated planar surface disposed at an angle of 45° to the axis of the rod. In use, the rod is aligned with the long shaft axis of the femur and attached to the femur at the greater trochanter. The rod is manipulated until the support arm and the long shaft axis of the tibia are disposed in the same plane. This procedure properly positions the elongated planar surface of the guide bar whereby an instrument in engagement with that surface traverses the femoral neck at an angle of 45° to the long shaft axis of the femur.

Another Whiteside U.S. Pat. No. 4,474,177 provides a method and apparatus for preparing the distal surface of a femur to receive a distal femoral prosthesis employing an intramedullary reamer which is used to internally locate the central long axis of the femur, an intramedullary alignment guide which is inserted into the space left in the intramedullary canal upon removal of the reamer and at least one femoral surface modifying instrument which cooperatively engages with a guide handle attached to the intramedullary alignment guide to accomplish the shaping of the distal femoral surface. The intramedullary alignment guide has a rod portion extending into the femoral intramedullary canal whose central long axis corresponds with the central long axis of the femur. The guide handle is attached to that rod portion at a preselected angle such that the shaping instruments fixed thereto assume the proper alignment with respect to the central long axis of the femur such that the distal femoral surface is shaped relative to that axis in a simple and accurate manner.

An improved triplanar knee resection system, disclosed in U.S. Pat. No. 4,487,203, provides a system for preparing a knee joint for a prosthesis. The apparatus of the triplanar knee system includes a single guide member for use in resecting the distal femoral condyles, the proximal tibia, and the distal femur. The guide member cooperates with a simplified set of instruments, including femur and tibia guide rods, a tibia adaptor, a tibia bar, and a femur bar, for establishing equal flexion and extension gaps and triplanar resections. The method of the triplanar knee system provides a simplified procedure for use by an orthopedic surgeon in properly preparing a knee joint for implantation of a prosthesis.

The Petersen U.S. Pat. No. 4,567,886 discloses a spacer guide for utilization in total knee surgery for establishing size of prosthesis and position of cuts for total knee replacement surgery includes a generally L-shaped base member for attachment to the anterior femoral cortex of a prepared femur with a generally L-shaped adjustable support member adjustably secured to the base support member and a vertically positionable indicator slide having a squaring jig for cooperative engagement and alignment with the cutting head of a tibia alignment and resection guide for squaring the tibia and femur and including indicator means for indicating the position of a tibia plateau cut and indicating the size and positioning for a distal femoral cut for indicating the sizing of the both the tibial and femoral prostheses.

The Kenna et al. U.S. Pat. No. 4,464,729 discloses a prosthetic knee implanted after cutting the femur and tibia with the aid of instruments which include axial alignment guides and a series of cutting jigs.

A method and apparatus for resecting a distal femoral surface is disclosed in U.S. Pat. No. 4,703,751 in which an intramedullary rod is inserted through the distal surface of the femur and along the femoral shaft access, leaving a protruding end; a jig is attached to the protruding end, the jig having a shaft for receiving the rod end and a support plate attached to an end of the shaft and extending parallel to the rod; attaching a reference bar to the shaft, the bar having a pair of opposing flanges and a central opening which receives the shaft therethrough, and adjusting the bar on the shaft such that the flanges contact condylar apeces of the femur; fixing the jig relative to the femur; attaching a cutting plate to the jig, the cutting plate having blade guides thereon, pivoting the cutting plate relative to the jig such that the blade guides made a predetermined angle with the rod, and securing the cutting plate to the jig; and inserting a saw blade through the blade guides to make a resection of the distal femoral surface. In the preferred embodiment, the shaft includes a plurality of bores along its length, each sized to receive the rod therethrough so that the distance between the rod and the support plate may be adjusted to accept different sized anterior femur portions. Also in the preferred embodiment, the apparatus includes a plurality of guide bars, each sized to space the blade guides a predetermined distance from the condylar apices.

The Kaufman et al. U.S. Pat. No. 4,721,104 relates to a surgical apparatus for providing an accurate recess in a distal femoral surface for the intercondylar stabilizing housing of a posterior-stabilized knee implant prosthesis which apparatus comprises a template having a bottom surface which is adapted to be placed in an aligning relationship with the flat surface of a distal femur which has been partially shaped to receive the femoral component of a posterior-stabilized knee implant prosthesis and a U-shaped slot passing through the template where the slot is of substantially the same size and shape as the outer periphery of the intercondylar stabilizing housing present on the femoral component to be implanted and a drilling means, preferably in the form of an endmill cutter, having a stop means thereon and the drilling means closely engages the sides of the U-shaped slot in the template so that the drilling means can be passed through the U-shaped slot until the stop means contacts a surface of the guide and is then drawn along the slot to create a precisely shaped and aligned recess in the femur for receipt of the intercondylar stabilizing housing. In a more preferred embodiment, the template is composed of a drilling means guide which fits over a femoral trial prosthesis which is used for trial reductions after the drill guide is used and removed.

The Russell et al. U.S. Pat. No. 4,722,330 relates to distal femoral surface shaping guide for mounting on a intramedullary alignment guide which references the central long axis of the femur in shaping the distal femoral surface and a method for shaping the distal femur using the shaping guide. The alignment guide of the present invention is adjustable relative to the surface of the anterior femoral cortex to insure that the anterior aspect of the distal femoral condyles is resected relative to that surface and, preferably, at the same level as that surface. The alignment guide of the present invention provides a main body which remains attached to the intramedullary alignment guide throughout the entire shaping of the distal femur. It thus requires fewer cutting guides and alignment steps than other shaping guides while allowing greater accuracy in shaping the distal femur relative to the central long axis of the femur.

An improved tibial cutting jig is disclosed in U.S. Pat. No. 4,736,737, provided for use in obtaining accurate tibial resection in the course of a total knee prosthesis implantation procedure. The tibial cutting jig includes a base for sliding reception onto an intramedullary alignment rod pre-installed generally along the longitudinal axis of the tibia. The base includes laterally extending outriggers carrying removable measurement keys of selected size for spacing the base above the tibial plateau by a selected dimension. An anterior saw guide depends from the base and is thus positioned relative to the tibial plateau in accordance with the sizes of the measurement keys.

The Buechel et al. U.S. Pat. No. 4,738,253 discloses a guide for a cutting device used to make a surgical cut in a first bone in desired spatial relationship with a pre-existing cut in a second bone is disclosed to include a means for contacting the pre-existing cut to establish a reference for the desired spatial relationship and a body member engaging the means for contacting and including a guide surface for establishing the desired spatial relationship and guiding a surgical cutting tool to cut the first bone in a plane which is not normally inclined with respect to the long axis of the first bone.

Another Buechel et al. U.S. Pat. No. 4,738,254 discloses a positioner for positioning a surgical instrument which acts as a guide for a cutting instrument which produces a surgical cut in an anatomical structure; in one embodiment the positioner positions a surgical instrument which acts as a guide for the cutting instrument at a predetermined position with respect to a previously resected surface whereby a further resection is made at a predetermined position with respect to the previously resected surface; and in a further embodiment the positioner acts as a adaptor for a surgical instrument which aids in producing surgical sections thereby allowing the surgical instrument to produce surgical cuts at various predetermined positions relative to a previous surgical cut made at one of several levels.

The Dunn et al. U.S. Pat. No. 4,759,350 provides a system of instruments for shaping the distal femur and proximal tibia surfaces to receive components of a knee prosthesis for knee replacement surgery. The system references the femur intramedullary channel with a femoral alignment guide to prepare the distal femur that, in turn, is a reference for several cutting guides for sequential attachment to the femoral alignment guide and prepared bone surfaces whereby the prepared distal femur is prepared to a flat surface that is perpendicular to the patient's mechanical axis with bone surfaces adjacent thereto sectioned to surfaces that are at right angles to that distal femur surface with chamfers therebetween to receive the femur component of a knee prosthesis. A tibial cutting guide is provided for preparing the proximal tibia that consists of a sleeve, with a tube telescoped therein, the ends thereof including pin arrangements for connecting them into the tibia, between the ankle and near the proximal tibia, an open tube end of the tibial cutting guide to receive a rod telescoped therein that mounts a cutting guide platform and includes a screw arrangement for releasably maintaining the road and tube together. The cutting guide platform includes a body with a saw guide slot formed therethrough to receive a saw blade to cut across the proximal tibia to form a surface for accommodating a tibial component of the knee prosthesis, the cutting guide platform body further including an arrangement for securing it to the tibia, slightly below the proximal tibia, and a tibial resection guide for setting a depth of cut across the proximal tibia.

U.S. Pat. No. 4,773,407 issued to Petersen discloses a method and instruments for resection of the distal femur. The instruments include a distal femoral resector and a femoral alignment guide/rod. The distal femoral resector is designed to be attached to the distal femur on a plane filed on the anterior femoral cortex. The distal femoral resector includes a feeler gauge laterally adjustable to adapt to the intercondylar notch of the particular patient and further includes a rotating rod having openings therethrough for fastening pins, which rotating rod is designed to facilitate the placement of the resector on the anterior femoral cortex in a flush manner. The femoral alignment guide/rod includes a plate insertable within a slot in the resector designed for the insertion of the cutting tool and further includes a pivotable rod which may be utilized to align the resector with the mechanical axis of the leg. The rod may then be pivoted to a position facilitating the insertion of a fastening pin through the resector. The method of operation using these instruments is also disclosed.

U.S. Pat. No. 4,892,093 issued to Zarnowski et al. discloses a cutting guide for guiding a saw blade during the preparation of a femur for the implant of the femoral component of a knee prothesis includes guide surfaces for enabling the cutting of all four of the anterior femoral cut, the posterior femoral cut, the anterior chamfer and the posterior chamfer, fully and completely, with certitude and accuracy, while the cutting guide remains located and secured to the femur in a single position on a transverse surface located along the distal femur.

The Dale et al. U.S. Pat. No. 4,893,619 discloses a device for guiding an osteotomy to be performed on the proximal end of a humerus that has a proximal saw guide alignable on a selected surface of the proximal end of the humerus for defining a saw line thereon; a radial arm connecting the saw guide to a distal mechanism for stably aligning the saw guide, the distal alignment mechanism has a pair of opposing lateral and medial epicondyle arms pivotally engagable with the lateral and medial sides of the distal end of the humerus, the epicondyle arms being pivotally mounted in a distal cross arm, the distal end of the radial arm being slidably mounted in the cross arm for distal to proximal slidable movement therein; the proximal end of the radial arm being rotatably connected to the saw guide through a proximal guide bar; the radial arm being supported above the humerus by the proximal guide bar and the epicondyle arms.

U.S. Pat. No. 4,907,578 relates to an improved method and instruments for a resection of the distal femur. The parent application discloses a femoral alignment guide/rod including a plate insertable within a guide slot in the resector which is also used for the guided insertion of a cutting tool. The present invention improves upon this structure by providing an auxiliary attachment member on the resector allowing attachment of a new femoral alignment guide/rod on the resector housing proximal to the cutting tool guide slot, which new guide/rod allows easier access to various resector components. In a further aspect, structure is provided allowing the use of the resector with an intramedullary rod to increase accuracy. In this aspect, a gauge is incorporated in the resector which allows compensation for the angle between the mechanical axis of the leg and the longitudinal extent of the internal cavity of the femur while also allowing compensation or correction for specific anatomical conditions such as, for example, valgus correction.

The Whiteside et al. U.S. Pat. No. 4,935,023 relates to a distal femoral surface shaping guide for mounting on an intramedullary alignment which references the central long axis of the femur in shaping the distal femoral surface and a method for shaping the distal femur using that shaping guide with particular applicability for shaping one condyle for attachment of a unicondylar prosthesis. The alignment guide of the present invention is adjustable relative to the surface of the condyle to insure that the distal femoral condyle is resected relative to that surface. The alignment guide of the present invention utilized visual sighting studs and provides a main body which remains attached to the intramedullary alignment guide throughout the entire shaping of the distal femur.

The Bowman et al. U.S. Pat. No. 4,952,213 discloses an apparatus for placing a bone cutting saw cutting guide adjacent a proximal surface of a human tibia bone having an elongated rod inserted into the tibia for clampingly supporting a rotating bar on the central longitudinal axis of the tibia bone. The bar being extended from the rod and connected to a pivot device which in turn is connected to a support arm that holds a saw cutting guide against a proximal portion of the tibia bone. The rotation angle of the rod determining the medial-lateral inclination of the saw cutting guide and the pivot device determining the anterior-posterior inclination of the saw cutting guide. The support arm is adjustable in length to determine the height of the saw cutting guide.

The Dunn et al. U.S. Pat. No. 4,959,066 provides an osteotomy guide assembly for femoral neck osteotomy and includes a saddle locator assembly and a saw guide attachment. The saddle locator assembly includes a barrel-shaped locating device that locates the saddle region of the proximal femur. The barrel further includes a transverse support bar extending from the barrel. The barrel is positioned over an intramedullary shaft which is temporarily positioned in and extends from the medullary canal of the femur. A saw guide is used in conjunction with a saddle locator assembly. The saw guide is attached to the support bar by a single locking means which provides for positional adjustment of the saw guide relative tot he support bar in two directions, including adjustment in the anterior-posterior direction along the transverse support bar and axially along the femur via a post which extends from the saw guide.

The Whiteside et al. U.S. Pat. No. 5,002,545 provides a shaping guide to permit accurate shaping of the tibial plateau while saving the anterior cruciate ligament. An alignment rod is located anterior to the anterior cruciate ligament and along the anterior cortex of the intramedullary canal of the tibia provides points of reference for all shaping operations. The shaping guide of the present invention is adjustable with respect to the handle portion of the rod so that the amount of resection of the tibial plateau can be controlled readily by the surgeon by raising or lowering of the cutting guide surfaces for resection of the tibia.

The Mikhail et al. U.S. Pat. No. 5,108,405 discloses a system for performing hip prosthesis revision surgery includes a trial femoral component having a passageway which, upon insertion in the cavity left after removal of the original prosthesis, provides guide means for drilling a channel to receive a guide wire which, upon removal of the trial femoral component, serves as guide means for progressively larger reamers.

SUMMARY OF THE INVENTION

The present invention provides an improved method and apparatus for implanting revision femoral and tibial prosthesis components. During knee joint placement surgery, surgeon first forms a plurality of cuts on the patient's distal femur and fits a femoral trial prosthesis to the surgically prepared distal femur.

The femoral trial prosthesis has an articulating surface for engaging a corresponding surface of a tibial prosthesis. The femoral trial also has a non-articulating surface that fits the patient's distal femur at the surgical cuts.

Using the method and apparatus of the present invention, the surgeon can build a custom "trial" tibial prosthesis to fit the patient's anatomy during revision surgery.

The femoral trial prosthesis has connections that allow the surgeon to fit wedge members to the prosthesis body.

The present invention provides instrumentation that assists a surgeon in a revision total knee case that has been previously implanted. The present invention can be used to solve a problem of loosening or pain or other like medical conditions.

As part of the method of the present invention, the surgeon removes the previous implant to expose the patient's bone tissue. In a revision case, the remaining bone has often degraded or been mechanically eroded.

With the apparatus of the present invention, the surgeon can not only shape the patient's bone to fit a knee implant but also uses the apparatus of the present invention to "trial" for the actual implant that would be put on that patient's knee as part of the revision surgery.

The apparatus of the present invention includes a prosthesis body that is generally J-shaped having a pair of condylar articulating surfaces including posterior and distal condylar articulating surfaces with a space therebetween. An anterior articulating surface is also provided on the trial body. The proximal side of the trial prothesis body has a plurality of flat intersecting surfaces. A plurality of wedge members of different size and shape can be attached to the proximal, non-articulating portion of the trial implant body. If the surgeon needs to place a particular wedge in order to accommodate for loss of bone for example, the surgeon would first place a wedge of selected size and shape on the trial prosthesis body. If that particular wedge fits properly, the surgeon would put the corresponding wedge on the final implant. The surgeon could implant the femoral component without any wedges if there was no need to fill in a recess or gap where bone had eroded. A surgeon could also put a wedge on either the medial or lateral side of the trial prosthesis and (the final implant) or the surgeon could have wedges on both sides.

The trial wedges can have different thicknesses. This allows the surgeon to pick the particular trial wedge that allows for the best fit.

Each wedge trial can provide a cutting edge. The femoral trial prothesis itself can also have a cutting edge. Often, the patient's bone will not correctly match the trial implant before the surgeon places the trial implant on the patient's bone. As the surgeon selects from a group of trial prosthesis bodies, one is selected that will actually be slightly smaller than the thickness of remaining bone. As the surgeon drives the trial onto the patient's distal femur, the cutting edges will actually remove bone in the exact places that it needs to be removed in order for the implant to fit snugly. Those cutting edges will cut bone as the trial is placed onto the patient's distal femur. In actual practice, there will not be an enormous amount of bone removed as the distal femur is already cut from the previous implant. The trial implant and its cutting surface simply removes a small bit of bone tissue so as to provide a snug fit.

The trial prosthesis body provides cutting guide slots that are on the anterior and/or posterior portion of the trial. These cutting guide slots allow the surgeon to prepare the distal femur if one or more wedges is to be used. During surgery, the surgeon first places the femoral trial on the patient's distal femur without any wedges being attached. If the femoral component does not seat properly, such as due to extra bone in the anterior chamfer portion, the surgeon can place a saw blade in the anterior chamfer slots in the femoral trial. The surgeon could remove some bone allowing the femoral component to seat properly. If there are some gaps where the wedges might be, the surgeon could use a saw blade into either a large or small slot that is parallel to the non-articulating surface that receives the trial wedge. These cutting guide surfaces are generally parallel and allow the surgeon to remove bone so when the particular selected wedge trial is placed on the trial prosthesis, it will be perfectly fitted. The surgeon uses the slots to "clean up" the bone on the distal femur if it is not perfectly matching up with the selected implant.

The thickness of each wedge should match the corresponding slot that is selected by the surgeon for cutting. The cuts can be made on the patient's distal femur using the cutting guide slots on the trial prosthesis. Typically, a vibrating saw such as a sagittal saw can be used. An osteotome can also be used.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is partial perspective view of the preferred embodiment of the apparatus of the present invention;

FIG. 2 is a partial frontal view of the preferred embodiment of the apparatus of the present invention;

FIG. 3 is a partial side view of the preferred embodiment of the apparatus of the present invention;

FIG. 4 is a perspective exploded view of the preferred embodiment of the apparatus of the present invention;

FIG. 5 is a perspective view of the preferred embodiment of the apparatus of the present invention;

FIG. 6 is a front view of the preferred embodiment of the apparatus of the present invention;

FIG. 7 is a bottom view of the preferred embodiment of the apparatus of the present invention;

FIG. 8 is a perspective view of the preferred embodiment of the apparatus of the present invention;

FIG. 9 is a side, lateral view of the preferred embodiment of the apparatus of the present invention;

FIG. 10 is a top view of the preferred embodiment of the apparatus of the present invention;

FIG. 16 is a partial perspective view of a first alternate embodiment of the apparatus of the present invention;

FIG. 17 is a partial frontal view of the first alternate embodiment of the apparatus of the present invention;

FIG. 18 is a partial side view of the first alternate embodiment of the apparatus of the present invention;

FIG. 19 is a partial perspective view of the second alternate embodiment of the apparatus of the present invention;

FIG. 20 is a partial frontal view of the second alternate embodiment of the apparatus of the present invention; and FIG. 21 is a partial side view of the second alternate embodiment of the apparatus of the present invention.

DETAILED DESCRIPTION OF THE PREFERRED EMBODIMENT

Figure 11:
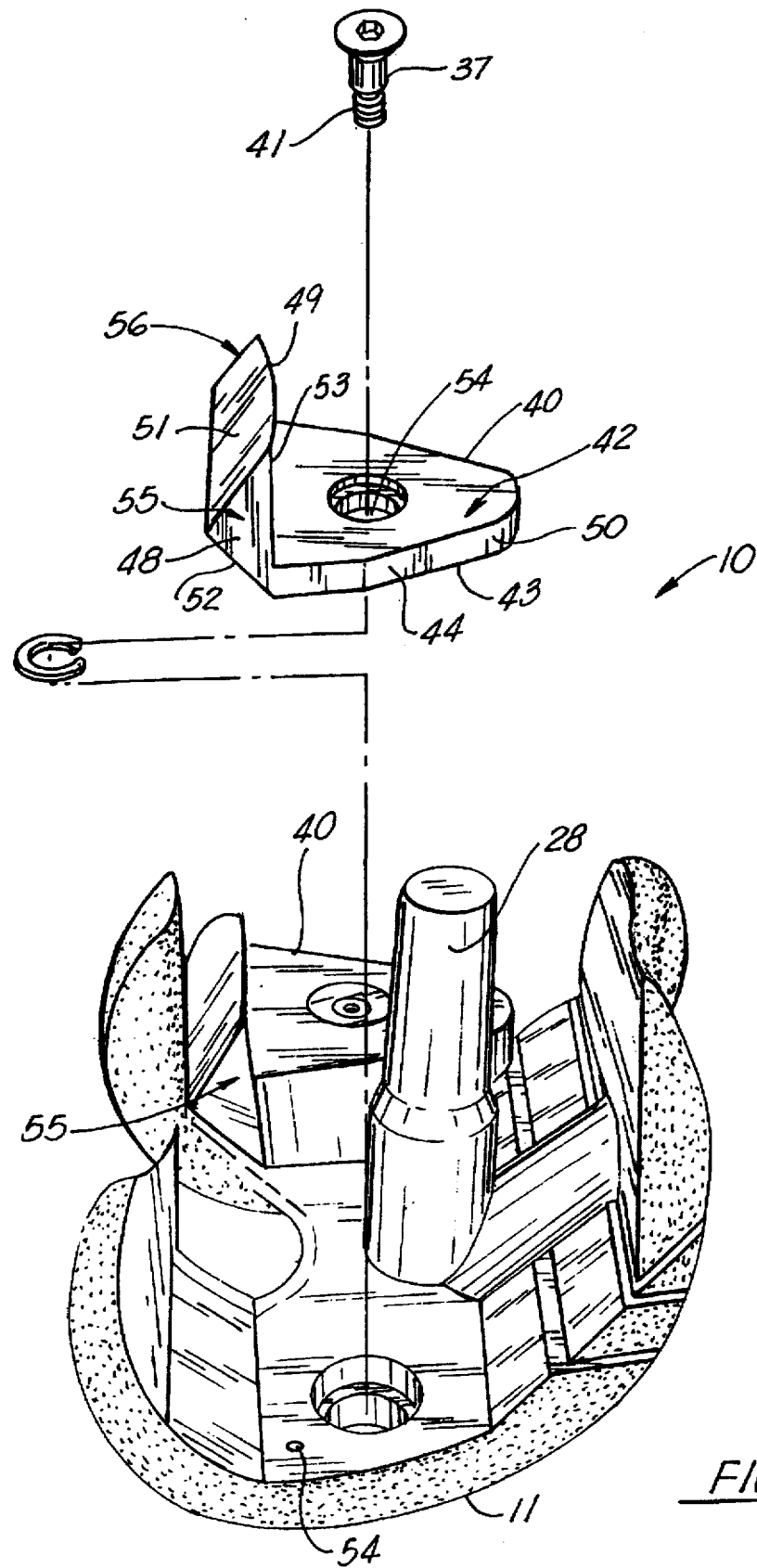
FIG. 11 is a perspective, exploded view of the preferred embodiment of the apparatus of the present invention.

In FIGS. 1-11, there can be seen the preferred embodiment of the apparatus of the present invention, designated by the numeral 10 in FIGS. 4-5 and 8-11. Trial femoral prosthesis 10 includes femoral prosthesis body 11 that is affixed to the patient's distal femur during knee replacement surgery. Body 11 includes an anterior portion 12, a pair of posterior condylar portions 13, 14 and a pair of distal condylar portions 15, 16.

The anterior portion 12 has an anterior articulating surface 17. The posterior condylar portions have posterior condylar articulating surfaces 18, 19. The distal condylar surfaces 15, 16 have respective distal condylar articulating surfaces 20, 21. A vertical line 22 extends from anterior articulating surface 17 towards distal condylar articulating surfaces 20, 21. The line 22 is a reference line that is used in combination with a similar reference mark on a tibial trial prosthesis. The surgeon rotates the tibial trial prosthesis tray until a corresponding mark on the tibial trial prosthesis tray lines up with the line 22 on the femoral trial prosthesis. These alignment lines such as 22 are preferably positioned during manufacture to maximize articulating contact between a femoral trial prosthesis 10 and a trial femoral prosthesis. Once the desired locations for the trial components are determined, the final implant components are placed in the same positions.

Figure 12:
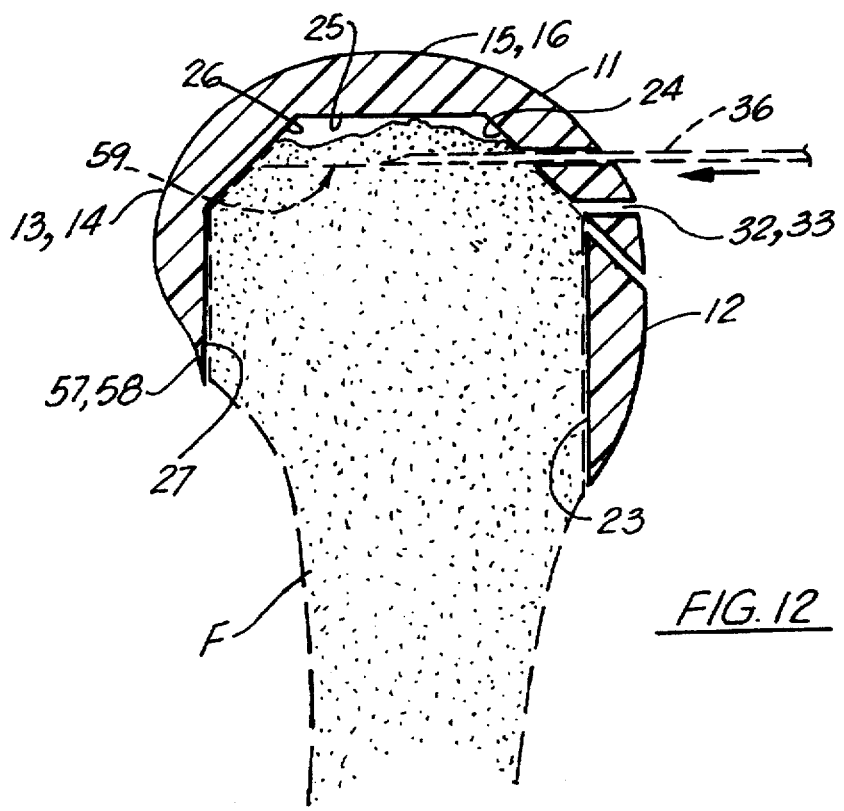
FIG. 12 is a schematic view illustrating the cutting of bone tissue from the patient's distal femur using the trial prosthesis body portion of the preferred embodiment of the apparatus of the present invention.

As shown in FIGS. 3 and 12, the prosthesis body 11 provides a number of non-articulating surfaces 23-27. These non-articulating surfaces 23-27 include an anterior flat non-articulating surface 23, a flat distal non-articulating surface 25, a flat posterior non-articulating surface 27, and a pair of chamfer non-articulating surface 24, 26. The surface 26 is an posterior non-articulating chamfer surface. The surface 24 is a non-articulating anterior chamfer surface.

A stem 28 extends from surface 25 upwardly along a vertical line that is generally parallel to the plane of surfaces 27 and 23. Stem 28 can be provided in different angles of valgus. An angulated thickened section 29 extends from stem 28 to non-articulating surface 23, functioning as a reinforcement to anterior portion 12 in the vicinity of several guide slots 30-35.

The cutting blade guide slots act as cutting guides 30-35 act as cutting guides for a saw blade 36 (or osteotome) used in cutting the patient's distal femur (See FIG. 12) to receive a trial wedge insert designated by the numeral 40 in FIG. 4. Insert 40 can be secured to the medial or the lateral side of non-articulating surface 25 using a bolt or screw 37 such as the countersunk screw 37 shown in FIG. 4. Openings 38, 39 are internally threaded openings that threadably connect with the threads 41 of screw 37 for example.

The plurality of cutting guide slots 30-35 include a plurality of medial slots and a plurality of lateral slots. The slots 30-31 are diagonally extending slots that are coplanar with the surface 24 as shown in FIG. 3. The slots 32 and 34 are parallel to one another and to surface 25 as shown in FIGS. 3 and 6. Surfaces 33, 35 are parallel to surfaces 25. In FIG. 2, the medial cutting surfaces are designated as 31, 33 and 35. The lateral cutting guide slots are designated as 30, 32, and 34.

In FIGS. 11 and 13-15, there can be seen more particularly the construction of a first wedge insert 40. The wedge insert 40 has an anterior section 50 and a posterior section 48. The anterior section 50 includes an upper surface 42 and a lower surface 43. The upper and lower surfaces 42, 43 are generally planar and parallel to one another. However, the lower surface 43 can have a peripheral raised portion 47 that can be used to engage a similarly shaped troth provided on surface 25 of trial prosthesis body 11.

Figure 13:
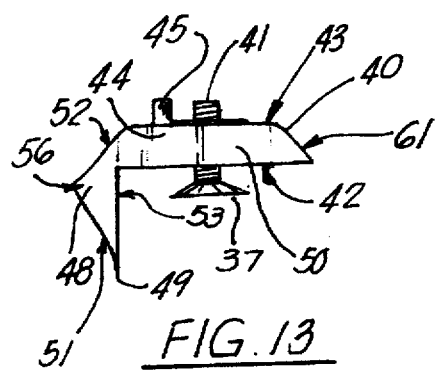
FIG. 13 is a partial side view of the preferred embodiment of the apparatus of the present invention illustrating one of the wedge insert portions thereof.
Figure 14:
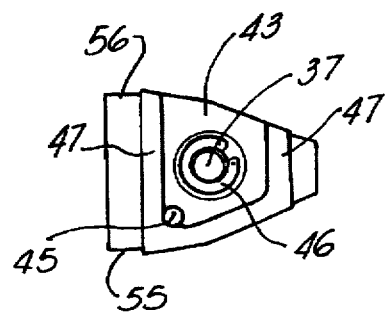
FIG. 14 is a bottom view of the wedge insert portion of the preferred embodiment of the apparatus of the present invention.

The lower surface 43 of anterior section 50 has a pin 45 that is cylindrically shaped as seen in FIG. 13. The pin 45 engages a similarly shaped opening 54 in body 11 at surface 25, as shown in FIG. 11.

Insert 40 also includes a posterior section 48 that carries a cutting edge 49 that is used in shaping the patient's distal femur F during placement of the trial prosthesis when wedges are to be used. Posterior section 48 has a plurality of flat surfaces 51-53, as shown in FIG. 11. Additionally, the posterior section 48 provides flat side surfaces 55, 56. The anterior section 50 has an inclined surface 61, that is generally parallel to the anterior chamfer surface 24 of the trial prosthesis 11 upon assembly, as shown in FIGS. 8-11. Similarly, the surface 52 of wedge insert 40 is generally parallel to the posterior chamfer surface 26 of the trial prosthesis body 11 upon assembly.

As with the cutting edge 49 of the wedge 40, the trial prosthesis body 11 can provide posterior condylar cutting edges 57, 58 associated with the condylar portions 13, 14, as shown in FIGS. 4 and 12 and/or an anterior cutting edge 61 associated with anterior portion 12 as shown in FIGS. 2-3. These cutting edges 57, 58, and 61 are on a proximal free end of the posterior and anterior surfaces, respectively, as shown in FIGS. 2,3, and 5 and help trim bone from the patient's distal femur in a revision case when the surgeon is applying the trial prosthesis body 11 to the distal femur after a previously implanted prosthesis has been removed.

In FIG. 12, the surgeon's saw blade 36 is shown tracking one of the selected guide slots 30-35. This allows the surgeon to trim bone along a desired line such as the line of cut indicated schematically as 59 in FIG. 12.

Figure 15:
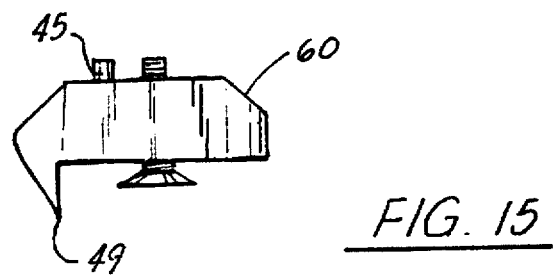
FIG. 15 is a side view of a wedge insert portion of the preferred embodiment of the apparatus of the present invention.

In FIG. 15, the wedge insert 60 is thicker than the insert of FIG. 13. If the surgeon desires to remove bone from a distal femur F by following the reference line 59 shown in FIG. 12, the surgeon would select either the cutting guide slot 34 or 35 (see FIG. 2). In such a case, less bone is being removed and therefore the surgeon would select a wedge insert 40. However, if the surgeon were to remove more bone, the surgeon would select the cutting guide slot 32 or 33 as shown in FIGS. 2 and 12. In this case, the surgeon would select the thicker wedge insert 60. It should be understood that other than thickness, the inserts 40 and 60 are the same.

FIGS. 16–18 show a first alternate embodiment of the apparatus of the present invention. The embodiment of FIGS. 16–18 provides the same trial prosthesis body 11 having an anterior portion 12, condylar portions 13, 14 and distal articulating portions 15, 16. The body 11 shown in FIGS. 16–18 can be used with inserts 40, 60 as with the embodiment of FIGS. 1–15. In the embodiment of FIGS. 16–18, an enlarged track 62, 63 is provided respectively for each condylar portion 13, 14. The tracks 62, 63 are generally rectangular in a cross section as shown in FIG. 18. This rectangular cross section allows an osteotome such as 64, 65 to be used to shave bone tissue from the patient's distal femur in a chamfer cut fashion. The non-articulating surface 26 of the prosthesis body 11 forms a portion of the tracks 62, 63. An elongated C-shaped slot 66 forms one side portion of each track. A similar C-shaped slot 67 forms an opposing side portion of the tracks 62, 63. During use, the surgeon can use either osteotome 64 or 65 with either track 62 or 63 respectively to shave bone tissue from the patient's distal femur.

In the embodiment of FIGS. 19–21, designated generally by the numeral 68, a trial prosthesis body 11 is shown having the same overall construction as that of the preferred embodiment, providing an anterior portion 12, a pair of condylar portions 13, 14, a distal articulating portion 15, 16, and a plurality of flat intersecting non-articulating surfaces 23, 27. In the embodiment of FIGS. 19–21, the trial prosthesis 68 includes medial and lateral posterior chamfer cutting slots 69, 70. In the embodiment of FIGS. 19–21, the surgeon can use either of the posterior chamfer cutting slots 69, 70 to track a saw blade during a trimming of the patient's distal femur at the non-articulating surface 26. As with the slots 30–35, the posterior chamfer cutting slots 69, 70 are spaced apart. Each posterior chamfer slot 69, 70 extends between an articulating surface 15, 16 and the non-articulating surfaces 25, 26.

The following table lists the parts numbers and parts descriptions as used herein and in the drawings attached hereto.

PARTS LIST

| Part Number | Description |
| --- | --- |
| F | femur |
| 10 | trial prosthesis assembly |
| 11 | prosthesis body |
| 12 | anterior portion |
| 13 | condylar portion |
| 14 | condylar portion |
| 15 | distal condylar portion |
| 16 | distal condylar portion |
| 17 | anterior articulating surface |
| 18 | articulating surface |
| 19 | articulating surface |
| 20 | articulating surface |
| 21 | articulating surface |
| 22 | reference line |
| 23 | non-articulating surface (anterior) |
| 24 | non-articulating surface (anterior chamfer) |
| 25 | non-articulating surface (distal) |
| 26 | non-articulating surface (posterior chamfer) |
| 27 | non-articulating surface (posterior) |
| 28 | stem |
| 29 | thickened section (canopy) |
| 30 | guide slot (lateral chamfer slot) |
| 31 | guide slot (medial chamfer slot) |
| 32 | guide slot (large wedge slot-lateral) |
| 33 | guide slot (large wedge slot-medial) |
| 34 | guide slot (small wedge slot-lateral) |
| 35 | guide slot (small wedge slot-medial) |
| 36 | saw blade |
| 37 | assembly screw |
| 38 | opening |
| 39 | opening |
| 40 | wedge insert (small) |
| 41 | threads |
| 42 | upper surface (of wedge) |
| 43 | lower surface (of wedge) |
| 44 | peripheral edge |
| 45 | pin |
| 46 | clip |
| 47 | raised portion (of lower surface) |
| 48 | posterior section |
| 49 | cutting edge (of wedge) |
| 50 | anterior section |
| 51 | surface (which creates cutting edge) |
| 52 | flat surface |
| 53 | flat surface |
| 54 | opening |
| 55 | side surface |
| 56 | side surface |
| 57 | cutting edge (of femoral trial) |
| 58 | cutting edge (of femoral trial) |
| 59 | reference line |
| 60 | wedge insert (large) |
| 61 | cutting edge |
| 62 | osteotome track |
| 63 | osteotome track |
| 64 | osteotome |
| 65 | osteotome |
| 66 | slot |
| 67 | slot |
| 68 | trial prosthesis |
| 69 | posterior chamfer cutting slot |
| 70 | posterior chamfer cutting slot |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A trial femoral prosthesis for use in knee joint replacement surgery comprising:
   a) a trim prosthesis body having an articulating surface and a non-articulating surface, said articulating surface including posterior medial and lateral condylar portions;
   b) a stem member that extends from the non-articulating surface;
   c) a trial insert that is connectable to the trial prosthesis body at the non-articulating surface on either the medial or lateral side of the trial prosthesis; and
   d) the trial prosthesis body having cutting surfaces on the medial and lateral condylar portions for cutting the patient's distal femur during a simultaneous placement of the trial prosthesis body on the patient's distal femur.

2. The trial prosthesis of claim 1 wherein the non-articulating surface includes multiple intersecting flat surfaces.

3. The trial prosthesis of claim 2 wherein one of the flat surfaces is an anterior chamfer non-articulating surface and the prosthesis body has a thickened portion on the anterior chamfer non-articulating surface that extends from a position adjacent the stem toward the anterior non-articulating surface.

4. The trial prosthesis of claim 2 wherein there are five non-articulating surfaces including distal, anterior, posterior, anterior chamfer and posterior chamfer surface.

5. The trial prosthesis of claim 4 further comprising a plurality of cutting guide slots that extend a partial distance through the trial body, each slot communicating with the articulating surface and a non-articulating surface.

6. The trial prosthesis of claim 5 wherein one of the cutting guide slots is parallel to the anterior chamfer non-articulating surface.

7. The trial prosthesis of claim 6 wherein there are two spaced apart cutting guide slots including medial and lateral slots that are coplanar with the anterior chamfer non-articulating surface.

8. The trial prosthesis of claim 7 wherein a plurality of the cutting guide slots are parallel to the distal non-articulating surface.

9. The trial prosthesis of claim 8 wherein there are two parallel cutting guide slots, each parallel to the distal non-articulating surface.

10. The trial prosthesis of claim 9 wherein there are a plurality of cutting guide slots that are parallel to the distal non-articulating surface at least medial and lateral slots, and wherein at least two of said cutting guide slots are parallel.

11. The trial prosthesis of claim 10 further comprising a cutting guide slot that is generally coplanar with the anterior chamfer surface.

12. The trial prosthesis of claim 5 wherein at least one of the cutting guide slots is parallel to the distal non-articulating surface.

13. The trial prosthesis of claim 12 wherein there are two spaced apart cutting guide slots including medial and lateral slots that are parallel to the distal non-articulating surface.

14. The trial prosthesis of claim 1 wherein the non-articulating surface includes a transversely extending distal non-articulating surface that intersects the patient's femoral intramedullary axis at a generally transverse angle when in use, and further includes a pair of generally parallel anterior and posterior surfaces, and wherein the stem generally tracks the patient's intramedullary axis.

15. The trial prosthesis of claim 14 wherein the non-articulating surface includes a posterior non-articulating surface and at least some of the cutting surfaces communicate with the posterior non-articulating surface.

16. The trial prosthesis of claim 14 wherein the non-articulating surface includes an anterior non-articulating surface and at least one of the cutting surfaces communicates with the anterior non-articulating surface.

17. The trial prosthesis of claim 1 wherein at least some of the cutting surfaces extend along a medial to lateral line.

18. The trial prosthesis of claim 1 further including anterior chamfer and distal cutting guide slots that each extend generally along a medial to lateral line, wherein the distal cutting guide slots are generally parallel to the distal non-articulating surface.

19. The trial prosthesis of claim 1 wherein the prosthesis body is generally J-shaped.

20. The trial prosthesis of claim 1 wherein the prosthesis body and trial insert have corresponding mating surfaces that abut upon assembly of the trial insert to the trial body.

21. The trial prosthesis of claim 1 further comprising a plurality of cutting guide slots that extend a partial distance through the trial body, each slot communicating with the articulating surface and the non-articulating surface.

22. The trial prosthesis of claim 21 wherein the cutting guide slots include opposed, spaced apart medial and lateral distal cutting guide slots for guiding a cutting tool for shaving bone tissue from the extreme distal surface of the patient's femur.

23. The trial prosthesis of claim 21 wherein the cutting guide slots each define a plane.

24. The trial prosthesis of claim 23 wherein at least two of the planes are parallel.

25. A trial femoral prosthesis for use in knee joint replacement surgery comprising:
   a) a trial prosthesis body having an (a distal) articulating surface and a (proximal) non-articulating surface, said articulating surface including medial and lateral condylar portions, said (distal) non-articulating surface including a plurality of flat intersecting surfaces that include distal, anterior chaffer and posterior chamfer surface;
   b) a wedge trial insert that is connectable to the trial prosthesis body at the (proximal) non-articulating surface and extending toward the anterior and posterior chamfer surfaces; (and)
   c) a plurality of cutting guide slots that extend through the trial body, each slot communicating with the articulating surface and the non-articulating surface; and
   d) the trial prosthesis body having cutting surfaces on the medial and lateral condylar portions for cutting the patient's distal femur during a simultaneous placement of the trial prosthesis body on the patient's distal femur.

26. The trial prosthesis of claim 25 wherein the cutting guide slots include at least one chamfer cutting slot that is coplanar with the anterior chamfer surface.

27. The trial prosthesis of claim 25 wherein the cutting guide slots include at least one distal slot for cutting the distal femur to accommodate the trial wedge.

28. The trial prosthesis of claim 25 wherein the cutting guide slots include at least one chamfer cutting slot that is coplanar with the posterior chamfer surface.

29. The trial prosthesis of claim 25 wherein the cutting guide slots include at least one posterior slot for cutting the distal femur to accommodate the trial wedge.

30. The trial prosthesis of claim 25 wherein the cutting guide slots include a pair of slots that, define generally parallel planes.

31. The trial prosthesis of claim 25 further comprising connection means for releasably connecting the wedge insert to the trial body prosthesis during surgery.

32. The trial prosthesis of claim 25 further comprising cutting edge means on the trial prosthesis body for cutting the patient's distal femur during placement of the trial prosthesis body on the distal femur.

33. The trial prosthesis of claim 25 further comprising cutting edge means on the trial wedge insert for cutting the patient's distal femur during placement of the trial prosthesis body and the wedge connected thereto on the distal femur.

34. The trial prosthesis of claim 25 further comprising cutting surfaces on both the trial femoral prosthesis body and the trial femoral wedge for cutting the patient's distal femur during surgical placement of the trial prothesis body on the distal femur.

35. The trial prosthesis of claim 25 wherein the wedge trial and trial body each provide planar non-articulating surfaces that abut upon assembly of a trial wedge to the trial body.

36. The trial prosthesis of claim 25 wherein the trial wedge has a first flat surface that fits to the prosthesis body and a second flat surface that fits the patient's surgically prepared distal femur.

37. The trial prosthesis of claim 36 wherein the second flat surface is generally parallel to a non-articulating flat surface on the trial body.

38. A trial femoral prosthesis for use in knee joint replacement surgery comprising:
 a) a trial prosthesis body having an (a distal) articulating surface and a (proximal) non-articulating surface, said articulating surface including medial and lateral condylar portions, said (proximal) non-articulating surface including a plurality of flat intersecting surfaces that include distal, anterior chamfer and posterior chamfer surfaces;
 b) a trial insert that is connectable to the trial prosthesis body at the (proximal) non-articulating surface and extending along a path spanning between the anterior and posterior chamfer surfaces;
 c) a plurality of cutting guide slots that extend through the trial body generally parallel to the distal surface (along a line that extends along an anterior to posterior line), each slot communicating with the articulating surface and the non-articulating surface;
 d) each of said cutting guide slots comprised of parallel flat surfaces that each define a plane; and
 e) the trial prosthesis body having cutting surfaces only on a proximal free end of at least one of the anterior and posterior surfaces for cutting the patient's distal femur during a simultaneous placement of the trial prosthesis body on the patient's distal femur.

39. The trial prosthesis of claim 38 and wherein the geometry, of the trial prosthesis corresponds to the size of an implant selected by the surgeon.

40. The trial prosthesis of claim 38 wherein there are a plurality of trial inserts of different sizes.

41. The trial prosthesis of claim 38 wherein there are a plurality, of trial inserts of different shapes.

42. The trial prosthesis of claim 38 wherein at least one of the slots forms an acute angle with an anterior/posterior line.

43. The trial prosthesis of claim 38 wherein one of the cutting guide slots is an osteotome track.

44. The trial prosthesis of claim 38 wherein one of the cutting guide slots is an osteotome track for cutting a posterior chamfer cut.

45. A trial femoral prosthesis for use in knee joint replacement surgery comprising:
 a) trial prosthesis body having an articulating surface and a non-articulating surface, said articulating surface including posterior medial and lateral condylar portions, said non-articulating surface including distal, anterior, posterior, anterior chamfer and posterior chamfer surfaces;
 b) a stem member that extends from the non-articulating surface; and
 c) the trial prosthesis body having a plurality of cutting guide slots thereon that are generally parallel to the distal non-articulating surface for guiding a cutting tool for cutting the patient's distal femur.

46. A trial femoral prosthesis for use in knee joint replacement surgery comprising:
 a trial prosthesis body having an articulating surface and a non-articulating surface, said articulating surface including posterior medial and lateral condylar portions, said non-articulating surface including distal, anterior, posterior, anterior chamfer and posterior chamfer surfaces;
 b) a stem member that extends from the non-articulating surface;
 c) the trial prosthesis body having a plurality of cutting guide slots thereon that are generally parallel to the distal non-articulating surface for guiding a cutting tool for cutting the patient's distal femur; and
 d) the cutting guide slots including medial and lateral slots that are parallel to the distal non-articulating surface.

47. The trial femoral prosthesis of claim 46 wherein there are two medial and two lateral cutting guide slots.

48. The trim femoral prosthesis of claim 46 wherein the cutting guide slot, include opposed, spaced apart medial and lateral distal cutting guide slots for guiding a cutting tool for shaving bone tissue from the extreme distal surface of the patient's femur.

49. The trial prosthesis of claim 46 further comprising a plurality of cutting guide slots that extend a partial distance through the trial body, each slot communicating with the articulating surface and a non-articulating surface.

50. The trial prosthesis of claim 46 wherein there are two spaced apart cutting guide slots including medial and lateral slots that are coplanar with the anterior chamfer non-articulating surface.

51. The trial prosthesis of claim 46 wherein the geometry of the trial prosthesis corresponds to the size of an implant selected by the surgeon.

52. The trial femoral prosthesis of claim 46 further comprising a trial insert that is connectable to the trial prosthesis body at a non-articulating surface.

53. The trial femoral prosthesis of claim 52 wherein the trial insert engages the distal, non-articulating surface.

54. The trial femoral prosthesis of claim 53 wherein the trial insert engages the posterior non-articulating surface.

* * * * *